(12) United States Patent
Matonick et al.

(10) Patent No.: US 11,885,735 B2
(45) Date of Patent: Jan. 30, 2024

(54) EX VIVO AND IN VIVO SYSTEMS FOR EVALUATING HEMOSTATIC PATCHES, SEALANTS, ADHESIVES ON SOLID ORGANS

(71) Applicant: Ethicon, Inc., Somerville, NJ (US)

(72) Inventors: John Matonick, Warren, NJ (US); Kevin Hengst, Phillipsburg, NJ (US); Matthew Pfefferkorn, Bridgewater, NJ (US); Robert J. Tannhauser, Bridgewater, NJ (US); Leo B. Kriksunov, Ithaca, NY (US)

(73) Assignee: Ethicon, Inc., Raritan, NJ (US)

( * ) Notice: Subject to any disclaimer, the term of this patent is extended or adjusted under 35 U.S.C. 154(b) by 1174 days.

(21) Appl. No.: 16/570,013

(22) Filed: Sep. 13, 2019

(65) Prior Publication Data
US 2021/0077654 A1    Mar. 18, 2021

(51) Int. Cl.
*G01N 19/00*    (2006.01)
*A61B 90/00*    (2016.01)
(Continued)

(52) U.S. Cl.
CPC ............. *G01N 19/00* (2013.01); *A61B 5/021* (2013.01); *A61L 15/32* (2013.01);
(Continued)

(58) Field of Classification Search
CPC .. G01N 19/00; A61B 5/021; A61B 2090/064; A61F 2240/008; A61K 49/00; A61L 2400/04
See application file for complete search history.

(56) References Cited

U.S. PATENT DOCUMENTS 6,733,774 B2    5/2004    Stimmeder
6,762,336 B1    7/2004    MacPhee et al.
(Continued)

FOREIGN PATENT DOCUMENTS

CN    203053795 U  *  7/2013
CN    109470822 A  *  3/2019  ............. G01N 19/00
(Continued)

OTHER PUBLICATIONS

Broekema, et al., In vitro analysis of polyurethane foam as a topical hemostatic agent, J Mater Sci Mater Med, Mar. 19, 2011, pp. 1081-1086, vol. 22 Issue 4.
(Continued)

*Primary Examiner* — Ryan D Walsh
(74) *Attorney, Agent, or Firm* — David R. Crichton; Leo B. Kriksunov

(57) ABSTRACT

The present is directed to systems for ex vivo testing performance of a hemostatic or sealing product attached to an animal organ and fully covering a cored channel in said organ, comprising: a pressure sensor positioned proximate to said hemostatic or sealing product in said cored channel; a monitoring or recording device configured to receive pressure readings from said pressure sensor; and a pressurized fluid source connected to said cored channel and configured to supply said pressurized fluid into said cored channel under constant or variable pressure. The present invention is also directed to methods of use for such systems.

16 Claims, 11 Drawing Sheets

(51) Int. Cl.
*A61L 15/32* (2006.01)
*A61B 5/021* (2006.01)
*A61K 49/00* (2006.01)

(52) U.S. Cl.
CPC ... *A61B 2090/064* (2016.02); *A61F 2240/008* (2013.01); *A61K 49/00* (2013.01); *A61L 2400/04* (2013.01)

(56) References Cited

U.S. PATENT DOCUMENTS

| | | | |
|---|---|---|---|
| 7,279,177 | B2 | 10/2007 | Looney |
| 8,846,105 | B2 | 9/2014 | Koopman |
| 9,439,997 | B2 | 9/2016 | Gorman |
| 2008/0213344 | A1 | 9/2008 | Mccarthy |
| 2010/0129427 | A1* | 5/2010 | Hen .................. A61L 15/28 424/445 |
| 2015/0297786 | A1 | 10/2015 | Riebman |
| 2020/0206472 | A1* | 7/2020 | Ma .................. A61B 34/37 |

FOREIGN PATENT DOCUMENTS

| | | | |
|---|---|---|---|
| EP | 0998311 B1 | 11/2003 | |
| EP | 1998311 A3 | 3/2010 | |
| EP | 2954778 A1 | 12/2015 | |
| WO | WO-0012004 A1 * | 3/2000 | ........... A61B 5/0215 |
| WO | 04/064878 | 8/2004 | |
| WO | WO-2014153566 A2 * | 9/2014 | ......... A61B 17/0057 |

OTHER PUBLICATIONS

Jesty, et al., Assessment In Vitro of the Active Hemostatic Properties of Wound Dressings, Journal of Biomedical Materials Research Part B: Applied Biomaterials, 2009, pp. 536-542, vol. 89 Issue 2.
Kheirabadi, et al., High-Pressure Fibrin Sealant Foam: An Effective Hemostatic Agent for Treating Severe Parenchymal Hemorrhage1, Journal of Surgical Research, 2008, pp. 145-150, vol. 144 Issue 1.

* cited by examiner

EX VIVO AND IN VIVO SYSTEMS FOR EVALUATING HEMOSTATIC PATCHES, SEALANTS, ADHESIVES ON SOLID ORGANS

FIELD OF THE INVENTION

The present invention relates to systems and methods for testing wound closure dressings and pads, surgical adhesives and sealants, more specifically to systems and methods for testing and evaluating performance and failure of hemostatic patches on animal solid organs as a function of blood pressure ex vivo and in vivo.

BACKGROUND

In a wide variety of circumstances, animals, including humans, can suffer from bleeding due to wounds or during surgical procedures. In some circumstances, the bleeding is relatively minor, and normal blood clotting functions in addition to the application of simple first aid are all that is required. In other circumstances substantial bleeding can occur. These situations usually require specialized equipment and materials as well as personnel trained to administer appropriate aid.

Bleeding during surgical procedures may manifest in many forms. It can be localized or diffuse from a large surface area. It can be from large or small vessels, arterial (high pressure) or venous (low pressure) of high or low volume. It may be easily accessible, or it may originate from difficult to access sites.

Conventional methods to achieve hemostasis include use of surgical techniques, sutures, ligatures or clips, and energy-based coagulation or cauterization. When these conventional measures are ineffective or impractical, adjunctive hemostasis techniques and products are typically utilized.

The selection of appropriate methods or products for the control of bleeding is dependent upon many factors, which include but are not limited to bleeding severity, anatomical location of the source and the proximity of adjacent critical structures, whether the bleeding is from a localized source or from a broader surface area, visibility and precise identification of the source and access to the source.

In an effort to address the above-described problems, materials have been developed for controlling excessive bleeding. Topical Absorbable Hemostats (TAHs) are widely used in surgical applications. TAHs encompass products based on oxidized cellulose (OC), oxidized regenerated cellulose (ORC), gelatin, collagen, chitin, chitosan, etc. To improve the hemostatic performance, scaffolds based on the above materials can be combined with biologically-derived clotting factors, such as thrombin and fibrinogen, or synthetic materials.

Many products have been developed as adjuncts to hemostasis. These products include topical absorbable hemostats (TAH) such as oxidized regenerated cellulose, gelatin in various forms with or without a thrombin solution, and collagen powder, as well as biologically active topical hemostatic products (topical thrombin solutions, fibrin sealants, etc.) and a variety of synthetic topical sealants. The control of bleeding as well as sealing of air and various bodily fluids is essential and critical in surgical procedures to minimize blood loss, to seal tissue and organ structures, to reduce post-surgical complications, and to shorten the duration of the surgery in the operating room.

In an effort to provide dressings with enhanced hemostatic and tissue sealing and adhering properties, therapeutic agents, including, but not limited to, thrombin, fibrin and fibrinogen have been combined with dressing carriers or substrates, including gelatin-based carriers, polysaccharide-based carriers, glycolic acid or lactic acid-based carriers and a collagen matrix. Examples of such dressings are disclosed in U.S. Pat. Nos. 6,762,336, 6,733,774, 9,439,997 and PCT publication WO 2004/064878 A1.

As discussed above, hemostasis involves the use of hemostatic patches, pads, sealants, as well as sutures, clips, staplers, surgical adhesives, and combinations of those devices. The design and assessment of these devices requires testing of the products in models that closely resemble the surgical in-vivo states of the tissue.

The current techniques for measuring blood pressure at an arbitrary defect site on the solid organ consists of measuring pressure at a remote location outside of the solid organ at one of the major arteries perfusing it. The blood vessels entering the solid organ branch multiple times and randomly throughout the tissue. Creating a defect at an arbitrary location on the solid organ results in cutting one or more of the blood vessels in a blind process. A decrease in the lumen of the arteries perfusing the defect site, relative to the main artery feeding the organ will result in a pressure drop. Ultimately the true pressure acting upon the hemostatic pad is unknown.

Slaughterhouse tissue, such as liver, spleen, and kidney are typically clotted and/or the blood vessels are filled with air. Pushing blood into the feeding arteries of the organ results in the blood clots and air being pushed deeper into the organ and blocking the blood flow. In addition, internal blood clots may become dislodged and migrate during the perfusion or applied tamponade, for some products, blocking the original blood flow and potentially resulting in false positives because the blood supply was internally stopped.

U.S. Patent Application Publication No. 20150297786A1 titled "Fenestrated Hemostatic Patch" discloses ex-vivo bench top circulatory cardiopulmonary bypass (CPB) model.

European patent publication EP998311B1 titled "HEMOSTATIC SANDWICH BANDAGE COMPRISING A THROMBIN LAYER BETWEEN TWO FIBRINOGEN LAYERS" discloses arterial hemorrhage rabbit aorta model in the rabbit.

U.S. Patent Application Publication No. 20080213344A1 tiled "Wound dressing and method for controlling severe, life-threatening bleeding" discloses that wound dressing formulations of candidate materials were then tested on the swine aortotomy model. Spleen laceration model was used to screen various dressings.

U.S. Pat. No. 7,279,177B2 titled "Hemostatic wound dressings and methods of making same" discloses hemostatic Performance of Different Materials in a Porcine Splenic Incision Model for hemostasis evaluation.

U.S. Pat. No. 8,846,105B2 titled "Dry powder fibrin sealant" discloses a liver scallop model on the liver of a pig.

European patent publication EP2954778A1 titled "ANIMAL MODEL FOR EVALUATING PERFORMANCE OF HEMOSTATIC AGENT FOR INDUCING HEMORRHAGE IN COMMON CAROTID ARTERY OR SUPERIOR SAGITTAL SINUS, AND USE THEREOF" discloses preparation of animal model (femoral artery) for evaluating hemostatic effects.

An article titled "In vitro analysis of polyurethane foam as a topical hemostatic agent", by Ferdinand Broekema et al., J Mater Sci Mater Med. 2011 April; 22(4): 1081-1086, discloses an experimental in vitro test model was used based on the Thrombostat 4000® (Von der Goltz, Seeon, Germany). It was used because of the possibility to insert different test materials in an existing model for measuring hemostasis in vitro. In the model blood flowed through the fixated test materials with a constant pressure of −40 mbar. Suction of the blood was performed through a needle with a diameter of 200 μm to create shear stress (FIG. 1). The shear stress was necessary to mimic capillary bleeding which is an important platelet activator in vivo. The thrombostat calculated the amount of blood flow through the test material over a period of 90 s. As a derivative for the extent of coagulation the blood flow deceleration was determined. This was calculated out of the blood volume that had passed the test material after 30, 60 and 90 s.

An article titled "High-Pressure Fibrin Sealant Foam: An Effective Hemostatic Agent for Treating Severe Parenchymal Hemorrhage", by Bijan Kheirabadi, et al., J Surg Res. 2008 January; 144(1):145-50, discloses that the left carotid artery was cannulated using PE-50 tubing and attached to a precalibrated pressure transducer. During the experiment, systolic, diastolic, and mean arterial pressure (MAP) and heart rate were continuously monitored and the data were collected by a computer for future analysis. A ventral midline incision approximately 20 cm long was made, and bleeding was controlled by electrocautery. Rabbits were hydrated with 10 mL/kg of lactated Ringer's (LR) solution supplemented with 2 mL sodium bicarbonate (8.4%) via IV drip during initial procedures. Following hydration, baseline MAP was recorded and rabbits were injected IV with 0.12 mL of danaparoid sodium (150 anti-Xa units) 5 min before liver injury.

An article titled "Assessment In Vitro of the Active Hemostatic Properties of Wound Dressings" by Jolyon Jesty, et al., J Biomed Mater Res B Appl Biomater, 2009 May; 89(2):536-42, discloses a method for assessing the active hemostatic properties of dressings in vitro, entailing measurement of the flow of recalcified platelet-rich plasma (PRP) through a dressing sample. If the dressing is hemostatically active, flow is reduced. This flow is then compared with the flow-through of PRP in which both platelet and coagulation function are blocked with EDTA. The ratio of the two generates a hemostatic index that ranges from 1.0 (no active hemostasis) to 0 (highly potent). The method is applicable to porous or semiporous dressings, whether fabric, sponge, fleece, or granules. For an active dressing, the test is easily modified to differentiate between the contributions of platelet and coagulation to overall hemostasis. The method is illustrated for fabrics, over-the-counter gauze and sponge dressings, collagen-based sheets, and an absorbent granule dressing. One active collagen dressing is used to illustrate discrimination between platelet and coagulation function. The ability to assess hemostatic properties may significantly enhance the development of advanced active dressings.

There is a need in advanced systems that enable testing of hemostatic products either ex vivo, i.e. in explanted model organs, or in vivo, i.e. in live animal models, under variable stress conditions that are similar or identical to in vivo environments, which enable precise control of the conditions of testing, such as applied pressure, for accurate evaluation of their performance.

BRIEF DESCRIPTION OF THE INVENTION

The present invention is directed to systems for ex vivo testing performance of a hemostatic or sealing product attached to an animal organ and fully covering a cored channel in said organ, comprising: a pressure sensor positioned proximate to said hemostatic or sealing product in said cored channel; a monitoring or recording device configured to receive pressure readings from said pressure sensor; and a pressurized fluid source connected to said cored channel and configured to supply said pressurized fluid into said cored channel under constant or variable pressure. The pressure sensor and monitoring or recording device can be wireless or connected by an electric cable. The pressure sensor can be positioned within 30 mm of said hemostatic or sealing product. The pressurized fluid source can comprise a perfusion system that is a peristaltic pump or gravity fed system. The pressurized fluid can be blood and the organ can be selected from liver, spleen, or kidney.

The system can further comprising a vacuum fixation table comprising: a body having a flat, contoured, or conformable upper surface and a vacuum channel within said body, said vacuum channel connected to a source of vacuum and terminating in a vacuum port on said upper surface, said vacuum port comprising one or more orifices or apertures on said upper surface; said body further comprising a fluid supply channel within said body that is connected to said pressurized fluid source and wherein said fluid supply channel terminates on said upper surface with a fluid exit port that is surrounded by said vacuum port. The vacuum fixation table can comprise a plurality of said vacuum ports and plurality of said fluid exit ports. cored channel is lined with a fluid-impermeable elongated hollow tubular liner sized to fit into said cored channel and into a portion of said fluid supply channel, with an optional spring installed into said fluid supply channel contacting said tubular liner.

The system can further comprise a vacuum fixation table comprising: a body having a flat, contoured, or conformable upper surface and a vacuum channel within said body, said vacuum channel connected to a source of vacuum and terminating in a vacuum port on said upper surface, said vacuum port comprising one or more orifices or apertures on said upper surface; wherein said system further comprises a pressurizing cannula connected to said pressurized fluid source and terminating with a sharp tip, and wherein said cored channel is a blind cored channel and said sensor is wireless. The pressure sensor can be positioned inside blind cored channel as a stand-alone unit or is attached to said pressurizing cannula proximate to said sharp tip. The pressurizing cannula can further comprise: an external tube that is coaxial and surrounds a portion of said pressurizing cannula; said external tube is connected to a source of vacuum, wherein a distal portion of said external tube proximal to said sharp tip is perforated. The blind cored channel can be lined with a pierceable liner.

The present invention is also directed to systems for in vivo testing performance of a hemostatic or sealing product attached to an animal organ and fully covering a blind cored channel in said organ, comprising: a pressurizing cannula connected to a pressurized fluid source and terminating with a sharp tip, a wireless or wired pressure sensor positioned proximate to said hemostatic or sealing product inside said blind cored channel as a stand-alone unit or attached to said pressurizing cannula proximate to said sharp tip, and a monitoring or recording device configured to receive pressure readings from said pressure sensor. The pressurizing cannula can further comprise: an external tube that is coaxial and surrounds a portion of said pressurizing cannula; said external tube is connected to a source of vacuum, wherein a distal portion of said external tube proximal to said sharp tip is perforated. The blind cored channel can be lined with a pierceable liner.

The present invention also relates to methods for testing a performance of a hemostatic or sealing product ex vivo, comprising: positioning a solid animal organ on an upper surface of a vacuum fixation table, said table having on said upper surface a vacuum port and a fluid exit port, fixating said organ on said vacuum fixation table by applying vacuum to said vacuum port, forming a cored channel through said organ in registration and in fluid communication with said fluid exit port; positioning a pressure sensor within said cored channel; supplying a fluid under pressure into said fluid exit port and into said cored channel; attaching said hemostatic or sealing product over said cored channel fully covering said cored channel; reading pressure measured by said pressure sensor in said cored channel by a monitoring or recording device configured to receive pressure readings from said pressure sensor; observing performance of said hemostatic or sealing product as a function of pressure and/or time; and optionally detecting failure or lack thereof of said hemostatic or sealing product by detecting rapid drop of pressure.

The present invention also relates to methods of testing performance of a hemostatic or sealing product in vivo, comprising: forming a blind cored channel in a solid organ; depositing into said blind cored channel a remotely readable pressure sensor; attaching said hemostatic or sealing product over said blind cored channel fully covering blind cored channel with said hemostatic or sealing product; reading pressure in said blind cored channel wirelessly by a monitoring or recording device configured to receive pressure readings from said pressure sensor; observing performance of said hemostatic pad as a function of pressure and time; and optionally detecting failure or lack thereof of said hemostatic pad by detecting rapid drop of pressure in said chamber.

The present invention also relates to methods of testing performance of a hemostatic or sealing product in vivo or ex vivo, comprising: forming a blind cored channel in a solid organ; inserting a pressurizing cannula connected to a pressurized fluid source and terminating with a sharp tip into said organ so that said sharp tip terminates inside said blind cored channel; using a wireless pressure sensor to measure pressure and report pressure to monitoring or recording device configured to receive pressure readings, said sensor positioned proximate to said hemostatic or sealing product inside said blind cored channel as a stand-alone unit or attached to said pressurizing cannula proximate to said sharp tip; supplying the pressurized fluid through said pressurizing cannula into said blind cored channel; attaching said hemostatic or sealing product over said blind cored channel fully covering blind cored channel with said hemostatic or sealing product; observing performance of said hemostatic or sealing product as function of pressure and/or time; and optionally detecting failure or lack thereof of said hemostatic or sealing product by detecting rapid drop of pressure in said blind cored channel. The methods can further comprise the step of inserting a pierceable liner into said blind cored channel. The methods can still further comprise the step of applying vacuum to an external tube that is coaxial and surrounds a portion of said pressurizing cannula, wherein a distal portion of said external tube proximal to said sharp tip is perforated. The methods, when used for ex vivo testing, can still further comprise the steps of: positioning said solid organ on an upper surface of a vacuum fixation table, said table having on said upper surface a vacuum port, and fixating said organ on said vacuum fixation table by applying vacuum to said vacuum port.

DETAILED DESCRIPTION

Figure 1:
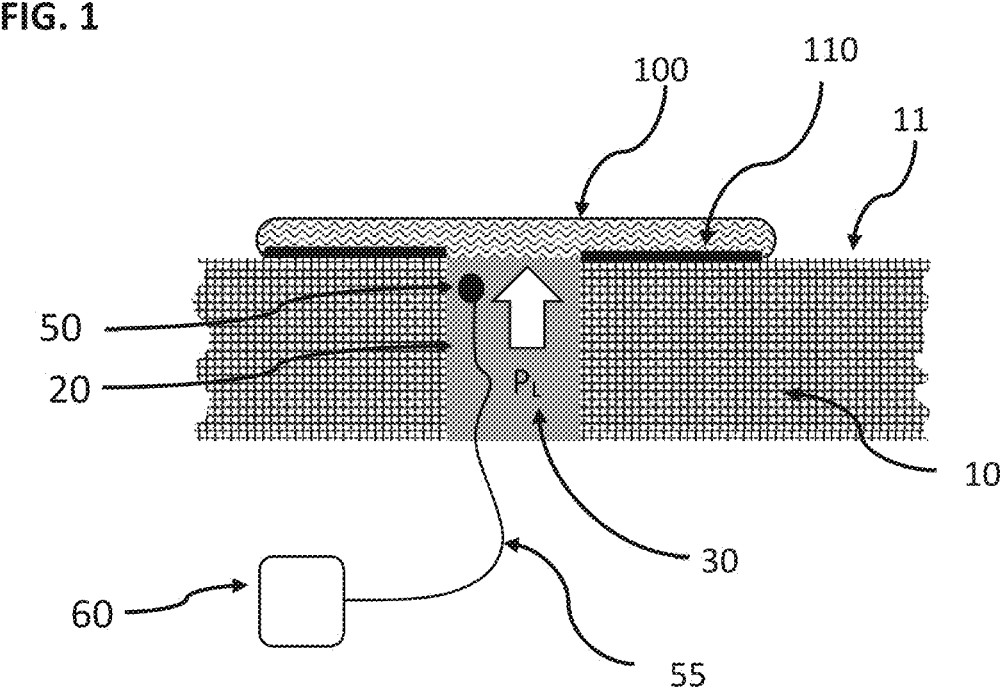
FIG. 1 shows an embodiment of the present ex-vivo solid organ hemostasis model in a schematic cross-sectional view.

The success of a topical hemostatic device, such as a patch or pad, is dependent on the adhesive and cohesive characteristics of the patch, being able to withstand underlying blood pressure applying stress to the underside of the patch at the wound or tissue defect site. The measurement and control of the local blood (or any other physiological fluid) pressure in a solid organ is extremely difficult leading to an uncertainty of the exact blood pressure that induces stress applied to the topical hemostasis patch. Embodiments of this invention relate to systems, devices, and methods for the precise measurement of the actual or local pressure acting on the topical hemostatic device before and optionally up to failure of said topical hemostatic device, as well as to fixation of animal organs under simulated or natural blood flow and under conditions close to natural anatomical and physiological tissue responses for the assessment and testing of wound closure or hemostatic devices. The success of a patch or pad is also very dependent on the application technique. The system describes a method of accurately controlling the application force through the use of pneumatic or hydraulic actuated tamponade devices. The devices apply a consist force and thus eliminate the variability of a manually applied material and the inconsistence between appliers.

The present ex-vivo and in vivo Solid Organ Hemostasis Model is an anatomical model used for the design and testing of hemostatic or sealing products whose mechanism of action is integrally related to the adhesive and cohesive strength of the product and bonding to the interface between the organ (i.e. spleen, kidney, liver or similar, or any animal organ tissue) and hemostatic or sealing product, such as patch, pad, cross-linkable hydrogel, and similar. The present systems and methods are applicable to testing any products related to wound closure and repair, such as hemostatic sealants, patches, fibrinogen and/or thrombin-based sealants and patches, fibrin glue, cyanoacrylate sealants, sutures, staples, etc., on animal organs of any type (incl. human). The model provides a means to accurately assess the performance as a function of applied stress (pressure) by knowing the surface area of the defect and the exact local pressure applied to the underside of the hemostatic or sealing product.

Advantageously, the present systems and methods provide an accurate determination of the impact of applied stress related to adhesive and cohesive failures because of accurate underlying pressure measurements. A pressure sensor or transducer is located where the fluid (such as blood) interacts with the hemostatic patch, thus providing direct pressure measurement of applied force to the product under test. Vacuum fixation of the underside of the solid organ provides sealing of a cored channel as a fluid pathway from leakage. The cored channel formed in the animal organ creates a standardized flow pathway for the testing fluid to the underside of the hemostatic patch. Advantageously, the present methods also provide for an immediate mechanism of testing, decreased tissue prep time from the slaughterhouse to test platform, provide consistency, verifiable presence of a lumen, a "no-touch" technique to the parenchyma thus maintaining the native cells to where the test article will be applied. The circular knife alignment system that is used to form the cored channel in the solid organ, provides a mechanism to align the defect and fluid flow pathway through the tissue to the underlying fluid flow supply pathway. The modularity of the test platform design allows the vacuum fixation region to be adjusted to the precise location of the solid organ being tested. The overall size and shape of each organ is different from animal to animal and by uniquely tailoring the test platform to fit the organ, it maintains multiple testing sites resulting in an increased throughput and decreased tissue prep time. The present system allows the solid organ to maintain its normal size and avoiding causing swelling and increasing shear stress to the hemostat pad.

According to the embodiments of the present invention, the pressure sensor or transducer is located immediately proximal to where the liquid interacts with the hemostatic patch providing a direct pressure measurement of the applied force to the patch under test. On the contrary, measuring fluid pressure remote to the defect site, through the native vascular, with a remote or external pressure gauge, leads to an uncertainty in the actual defect site pressure applied to the hemostasis product as will be shown in later text and Figures, such as FIG. 6. The arterial network within a solid organ is made up of a network of progressively smaller diameter arteries leading to a network of capillary beds in a random layout of arteries from one organ to the next. As per the present system, the defect on the surface of the solid organ is formed to create bleeding and provide a testing site for the hemostasis product with the pressure sensor positioned locally in the immediate vicinity. Such system and method are blind to the underlying vasculature, with the ability to cut any unknown size or number of arteries or veins without affecting the precision and location of pressure measurements.

The Ex-Vivo and In Vivo Solid Organ Hemostasis Model is an anatomical model used for the design and testing of hemostasis products whose mechanism of action is integrally related to the adhesive and cohesive strength of the product and bonding to the cell layer interface between the organ (i.e. spleen, kidney, liver, or similar) and tested product such as sealing/hemostatic patch. The model provides a means to accurately assess the performance as a function of applied stress by knowing the surface area of the defect and the exact, local pressure applied to the underside of the applied patch product. Existing or novel mechanisms of hemostasis or sealing may be assessed with this system rapidly and reproducibly. The system provides an anatomical platform for evaluating hemostasis pad type design concept attributes such as application techniques, burst pressure, cohesive performance, adhesive performance, overlap region, and static, stepped, and/or pulsed blood flow conditions.

Referring to FIG. 1, in one embodiment, the ex-vivo solid organ hemostasis model is designed to assess the hemostatic performance of prototype and competitive patch products in isolated blood perfused organs with exact pressure measurements. FIG. 1 shows a schematic cross-sectional view of solid organ 10 (such as spleen, liver, and the like), having cored channel 20 formed within organ 10 and filled with pressurized fluid 30, which is preferably blood, but can be any physiological fluid or even water or saline. Cored channel 20 is formed by using known tools to form well defined channel in organ 10, most typically channel 20 is a cylinder-shaped channel formed by removing a cylinder-shaped plug of tissue by using a tubular coring tool comprising a hollow tube with a sharpened end. Hemostatic or sealing patch 100 is shown applied on top surface 11 of organ 10 and adhering to top surface 11 in the areas of adherence 110 where tissue of organ 10 and patch 100 interface each other and are in direct contact.

FIG. 1 shows channel 20 filled with fluid 30 under local pressure indicated by letter "$P_L$" and also schematically showing by the arrow how the pressure of fluid 30 is directed against patch 100 with the point of applied pressure shown. Pressurized fluid 30 can affect lifting or cracking of pad 100 which indicates failure of pad 100. The objective of the test and model is to develop pad 100 that is capable of withstanding a given local pressure $P_L$ of fluid 30 and also verify performance of pad 100 under reproducible ex vivo models (and in some cases in vivo animal models).

Also shown is pressure transducer, sensor, or detector 50, which can be wired, as shown, with cable 55 connecting pressure sensor 50 to monitoring or recording device 60. In other embodiments, pressure sensor 50 is wireless and cable 55 is optional or not needed.

According to embodiments of the present invention, pressure sensor 50 is located proximal to pad 100 inside channel 20, such as within 0-50 mm distance from pad 100, such as touching pad 100, within 0, 1, 5, 10, 15, 20, 25, 30 mm from pad 100, most preferable within 3-30 mm distance from pad 100.

According to the present solid organ hemostasis model, local fluid (blood) blood pressure $P_L$ is measured at the defect site, as shown in FIG. 1, whereby pressure sensor 50 is located proximal to pad 100 inside channel 20.

The inventors have discovered that local fluid pressure ($P_L$) may be significantly different vs. pressure measured remotely, remote blood pressure ($P_R$) because of the smaller diameters of the vascular branching network within the solid organ and other issues, such as leaking, bleeding, air emboli, blood clots, etc.

Figure 2:
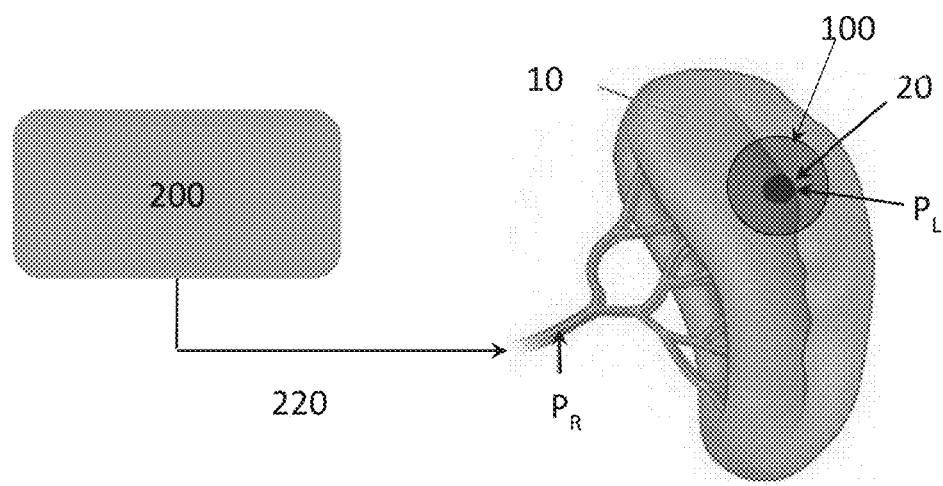
FIG. 2 schematically shows Pressure Measurement Locations for the present model and for alternative measurements.

Referring to FIG. 2, further illustrated are Pressure Measurement Locations. Organ 10 (such as spleen shown as an example only) is ex vivo perfused with fluid, such as blood from perfusion system 200 (such as pump or gravity flow system) and supplies fluid into organ 10 via flow line 220. In some embodiments, constant pressure gravity feed system can be controlled for constant static pressure or constant linearly or step-wise increasing pressure. Pressure can be applied using any curve (such as hyperbolic, step up/down, etc.). In some embodiments, a pressure controller can be utilized in the system, based on feedback from local pressure measurement or can operate based on elapsed time. Pulsed pressure wave shapes may also be utilized.

Defect site or channel 20 is shown covered by pad 100, proximal to which local pressure $P_L$ is measured. The Remote Pressure ($P_R$) can be measured through the native arteries away from the defect as shown. The remote pressure may be substantially different compared to local pressure measured at the defect site (Local Pressure ($P_L$)). The uncertainty of the actual local pressure value makes it impossible to truly know what pressure is acting on the pad 100 if the data from remote pressure monitoring is used.

Figure 3:
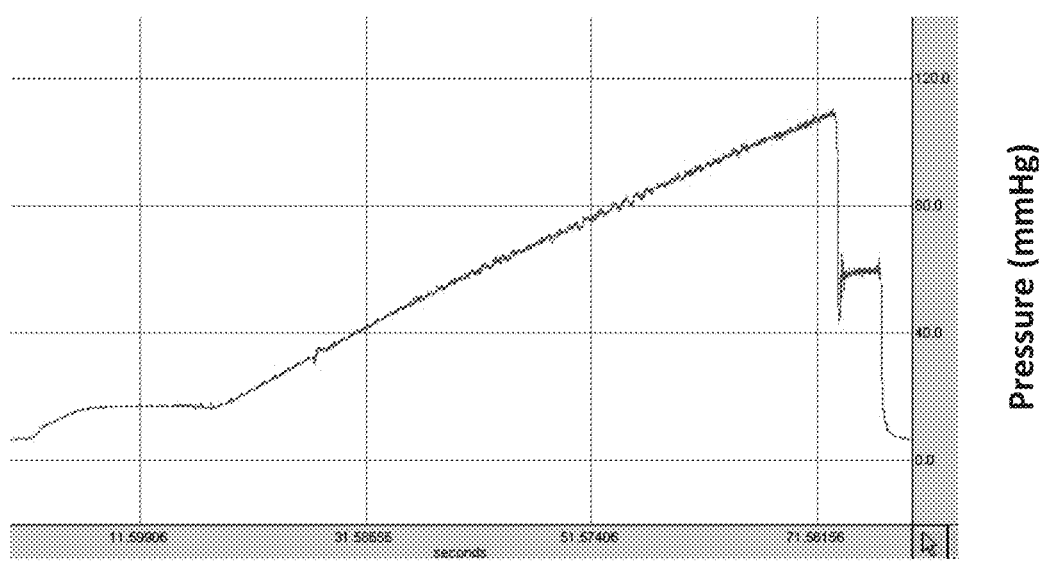
FIG. 3 shows a graph of typical pressure response curve of the model, or output of pressure sensor data recorded when pressure $P_L$ is steadily increasing over time.

Referring to FIG. 3, a typical pressure response curve of the model, or output of pressure sensor 50 data recorded when pressure $P_L$ is steadily increasing over time is shown. The graph demonstrates in coordinates Pressure $P_L$ (mm Hg) vs. time (s) that as fluid 30 is being supplied into channel 20 under increasing pressure, $P_L$ steadily increases. At the point of failure of pad 30, which point is visible in the right side of the graph as a sharp drop in pressure observed at about 110 mm Hg (highest pressure achieved). The drop in pressure indicates that pad 100 has separated from organ 10 resulting in immediate pressure drop. Thus, this test demonstrated pad 100 capable of withstanding pressures up to about 110 mm Hg. Recording the applied pressure at the failure point is then used in characterizing and or developing pad 100.

Figure 4:
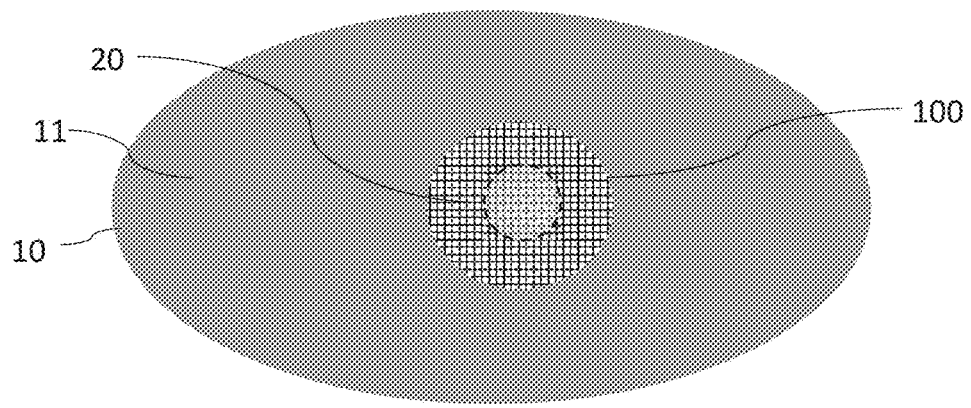
FIG. 4 shows a schematic top view of solid organ.

Referring to FIG. 4, a schematic top view of organ 10 is shown with channel 20 shown in dashed lines covered by patch 100 attached over organ 10 top surface 11 and fully covering channel 20. The present model system evaluates cohesive stress (typically for a cohesive failure)

$$\text{Stress} = \sigma = \frac{P_L}{A_{20}}$$

applied to the patch 100 as a function of local pressure $P_L$ applied to underside of patch 100 over the channel 20 surface area, $A_{20}$, to which pressure is applied.

The present model system also evaluates adhesive stress applied to the patch 100 as a function of local pressure $P_L$ applied to underside of patch 100 over the surface areas of adherence 110, $A_{110}$, where tissue of organ 10 and patch 100 interface each other and are in direct contact.

$$\text{Stress} = \sigma = \frac{P_L}{A_{110}}$$

Figure 5:
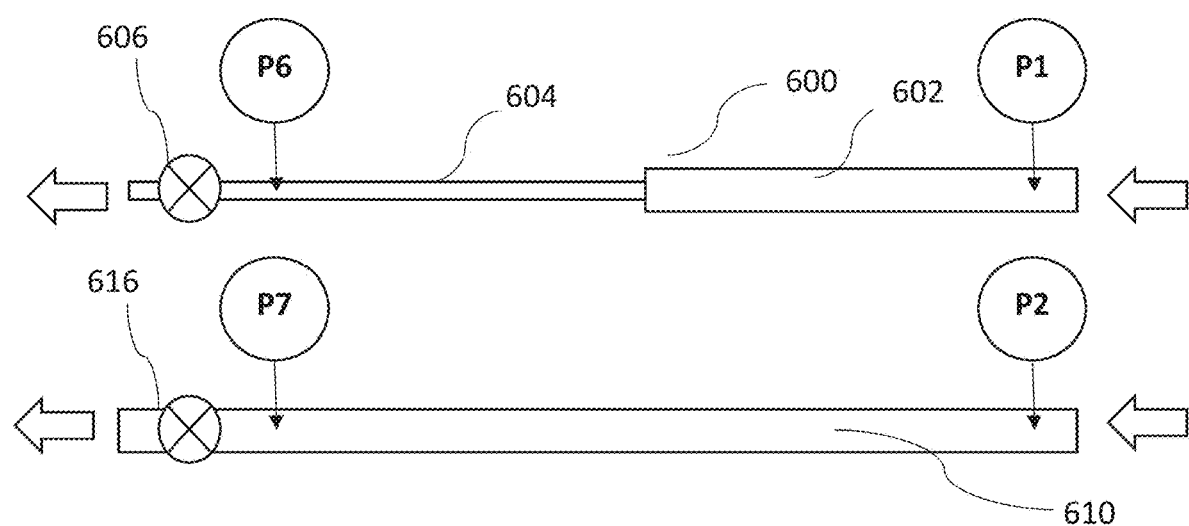
FIG. 5 shows a schematic representation of the test setup comparing two flow conduits.

Testing of Variability of Measured Pressure Dose to the Patch Testing Point Vs. Remote from the Patch Testing Point Referring to FIG. 5, where a schematic representation of the test setup is presented, the inventors have performed a test whereby a model comparing two flow conduits was tested. Polymeric tubing 600 has a first portion 602 of larger diameter and a second portion 604 of smaller diameter. Polymeric tubing 610 is all the same diameter equal to diameter of first portion 602. Model fluid (water) was infused into tubing 600, 610 as shown by arrows pointing into tubing on the right side of the diagram. Pressure P1 was measured as shown close to fluid infusion into tubing 600 and pressure P2 was measured as shown dose to fluid infusion into tubing 610. Fluid then flowed into tubing 600, 610 and either a) reached a static condition when valve 606 at the exit of tubing 600 and valve 616 at the exit of tubing 610 were closed, or b) was at a dynamic or flowing condition, with fluid exited tubing 600, 610 as shown by arrows pointing out of tubing on the left side of diagram when valves 606 and 616 were open. Pressure P6 was measured as shown close to fluid exit before valve 606 and pressure P7 was measured as shown close to fluid exit before valve 616.

Figure 6:
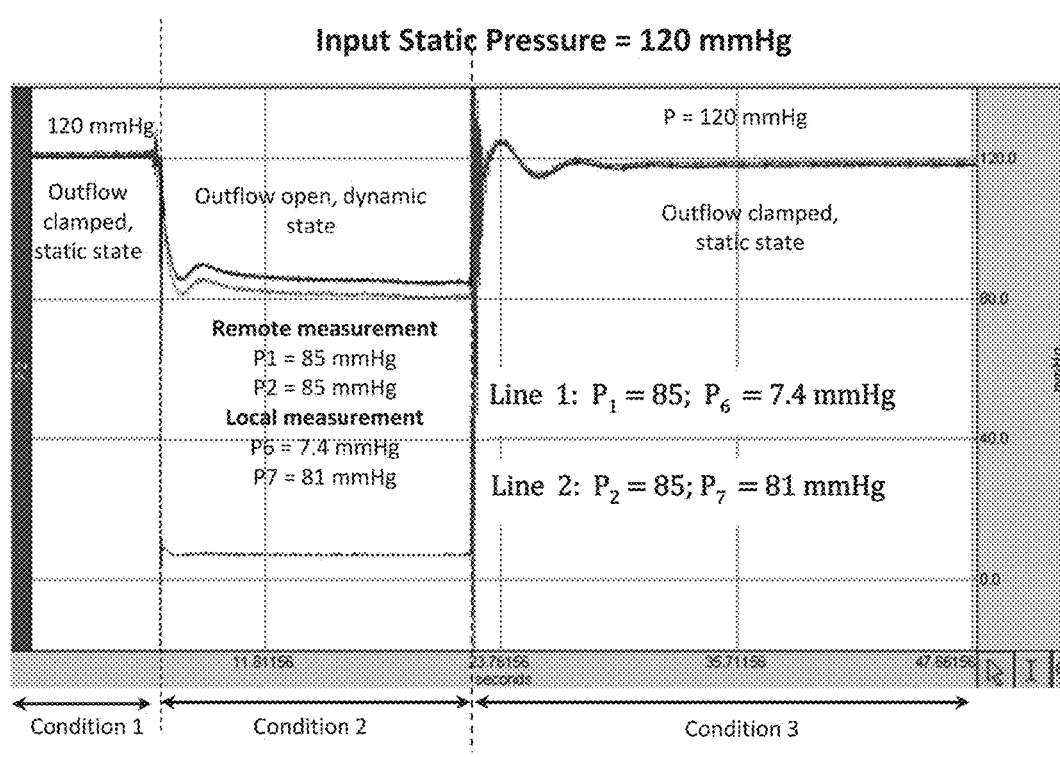
FIG. 6 shows the results of the measurement using the setup of FIG. 5.

FIG. 6 shows the results of this measurement, with pressures P1, P2, P6, P7 plotted vs. time at three different conditions. Condition 1, as shown on the left side of the chart at the beginning of the test corresponds to the valves 606 and 616 closed, i.e. static condition. As seen, at condition 1 remote pressure P1, P2 which are close to fluid infusion and local pressures P6, P7 measured are identical P1=P2=P6=P7=120 mm Hg. However, at condition 2, shown at the intermediate time in the center of the chart, when fluid is allowed to flow by opening valves 606, 616, there is a significant divergence in remote pressures P1, P2 and local or proximal or leak pressures measured as P6, P7, which were highly dependent of the diameter of the conduit. As seen, at condition 2 remote pressures P1=P2=85 mmHg while local pressure P6=7.4 mmHg and P7=81 mmHg.

At condition 3, which is equal to the condition 1, or static condition, and shown on right side of the chart, the system returns to the initial pressure situation whereby all pressures are identical. This demonstrates the importance of measuring $P_L$ when evaluating hemostatic products on in vivo or explanted animal organs. This illustrates the mistakes that can be made by using a remote pressure measurement external to the solid organ where blood vessels reduce in lumen diameter and the impact is significant, to the fourth order.

The vessel lumen in the solid organ can be reduced by a natural tapering of the anatomy or by partial occlusion from blood clots or air emboli.

Embodiments for Ex Vivo Testing of Hemostatic and/or Sealing Patch

Figure 7:
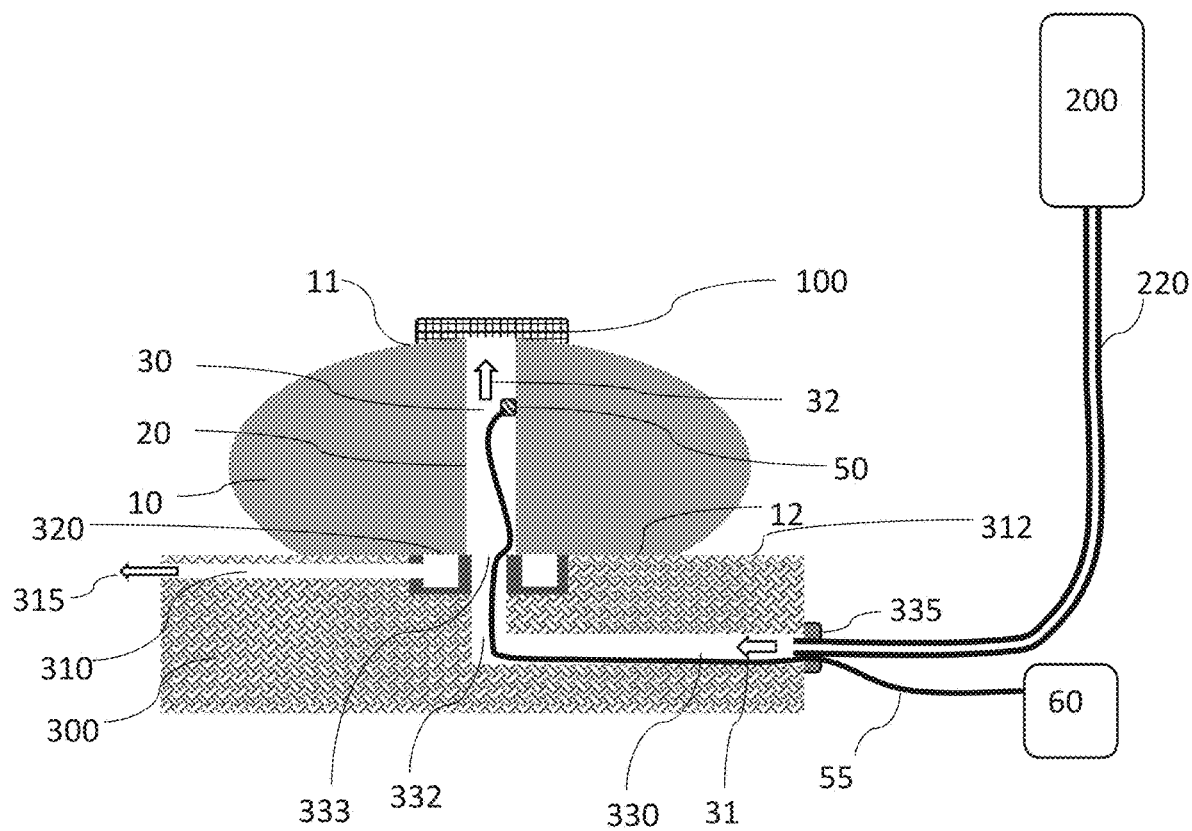
FIG. 7 shows a schematic side cross-sectional view of an embodiment of the present system.

Referring to FIG. 7, schematic cross-sectional view of an embodiment of the present system is presented, showing organ 10 positioned on vacuum fixation table 300, with lower surface 12 of organ 10 in contact with upper surface 312 of table 300 and top surface 11 of organ 10 exposed opposite table 300 for testing. Upper surface 312 of table 300 can have a flat, contoured, or conformable (static or dynamically) upper surface.

Table 300 has a vacuum channel 310 connected to a source of vacuum (not shown) such as a pump, vacuum channel 310 terminating in vacuum port 320 on upper surface 312 of table 300 for applying vacuum to organ 10 lower surface 12. Vacuum applied to channel 310 is schematically shown by evacuation arrow 315. Vacuum port 320 comprises one or more orifices or openings on upper surface 312 of table 300, such as formed by a plurality of apertures or one ring-shaped opening. Application of vacuum to channel 310 results in vacuum assisted fixation of organ 10 on upper surface 312 of table 300 and immobilizing of organ 10 for further testing.

Table 300 has a fluid supply channel 330 which is connected to perfusion system 200 (such as pump or gravity flow system, as shown) at port 335 and supplies fluid 30 into fluid supply channel 330 and into organ 10 via flow line 220. Arrow 31 indicates flow of fluid 30 in channel 330. Vertical portion 332 of channel 330 terminates on upper surface 312 of table 300 with fluid 30 exit port 333, which is surrounded by vacuum port 320 (optionally coaxial to vacuum port 320).

Exit port 333 is aligned and in registration with cored channel 20 formed within organ 10, so that fluid 30 flows as shown by arrow 31 in channel 330, then can flow into vertical portion 332, exit through exit port 333 the table 300 and enter cored channel 20 flowing as schematically shown by arrow 32. On top surface 11, pad 100 is shown adhering to organ 10 and positioned to fully cover cored channel 20.

The diameter of vertical portion 332 of channel 330 when it terminates on upper surface 312 of table 300 can be equal to diameter of the cored channel 20, smaller than diameter of cored channel 20, as shown, or up to 30% larger than diameter of cored channel 20. In a preferred embodiment, diameter of vertical portion 332 of channel 330 is equal to or smaller than diameter of cored channel 20, and is from 10% to about 100% of diameter of cored channel 20, such as 20%, 30%, 40%, 50%, 100% of diameter of cored channel 20.

Pressure sensor 50 is located proximal to pad 100 inside channel 20 and is connected via cable 55 to monitoring or recording device 60. In another embodiment, pressure sensor 50 is wireless and cable 55 is optional or not needed (not shown). Cable 55 is shown routed through fluid supply channel 330 and vertical portion 332. Alternatively, it can be routed through a separate channel (not shown).

Figure 8:
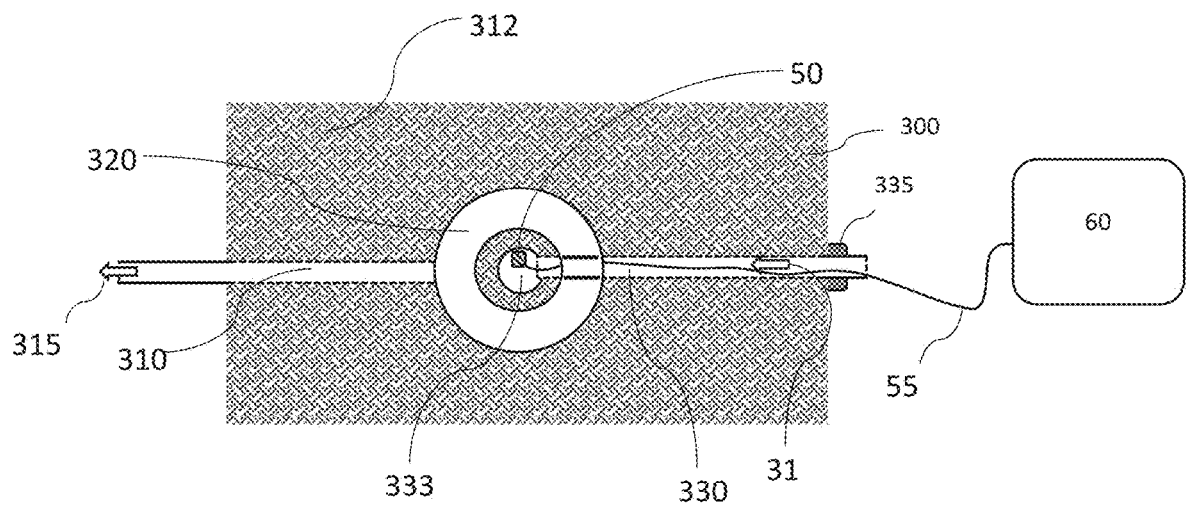
FIG. 8 shows a schematic top view of an embodiment of the present system.
Figure 9:
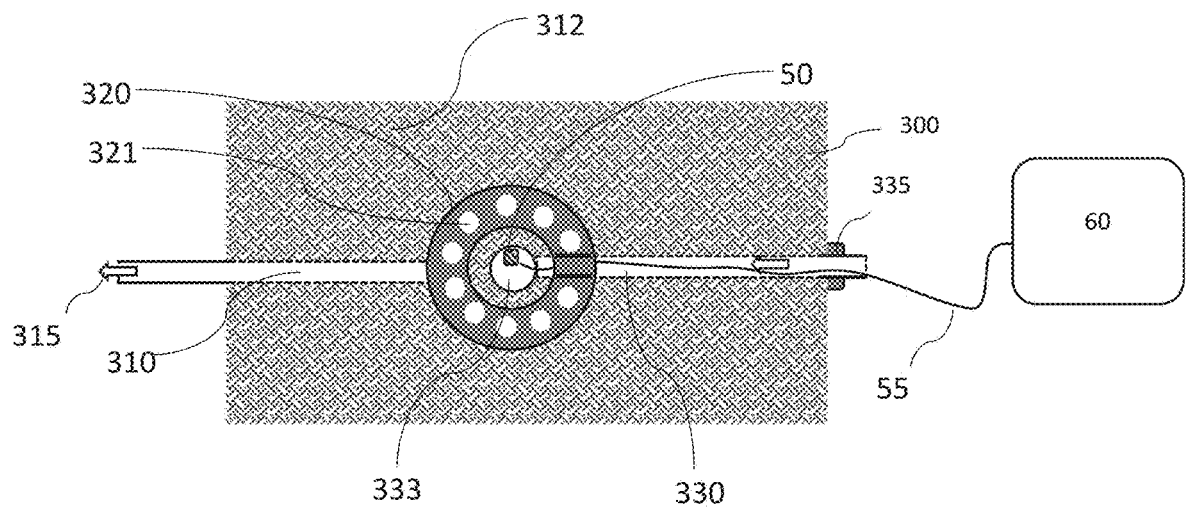
FIG. 9 shows a schematic top view of an embodiment of the present system.

Referring to FIGS. 8 and 9, a schematic top view of an embodiment of the present system is presented, with embodiments similar to presented in FIG. 7 shown, without showing organ 10 and patch 100. Vacuum fixation table 300 is shown from top surface 312, with fluid supply channel 330 running inside table 300 shown in dotted lines. Vacuum channel 310 running inside table 300 is shown in dotted lines.

FIG. 8 shows vacuum port 320 comprising one ring-shaped opening. FIG. 9 shows vacuum port 320 comprising plurality of orifices or openings 321 on upper surface 312 of table 300.

Figure 10:
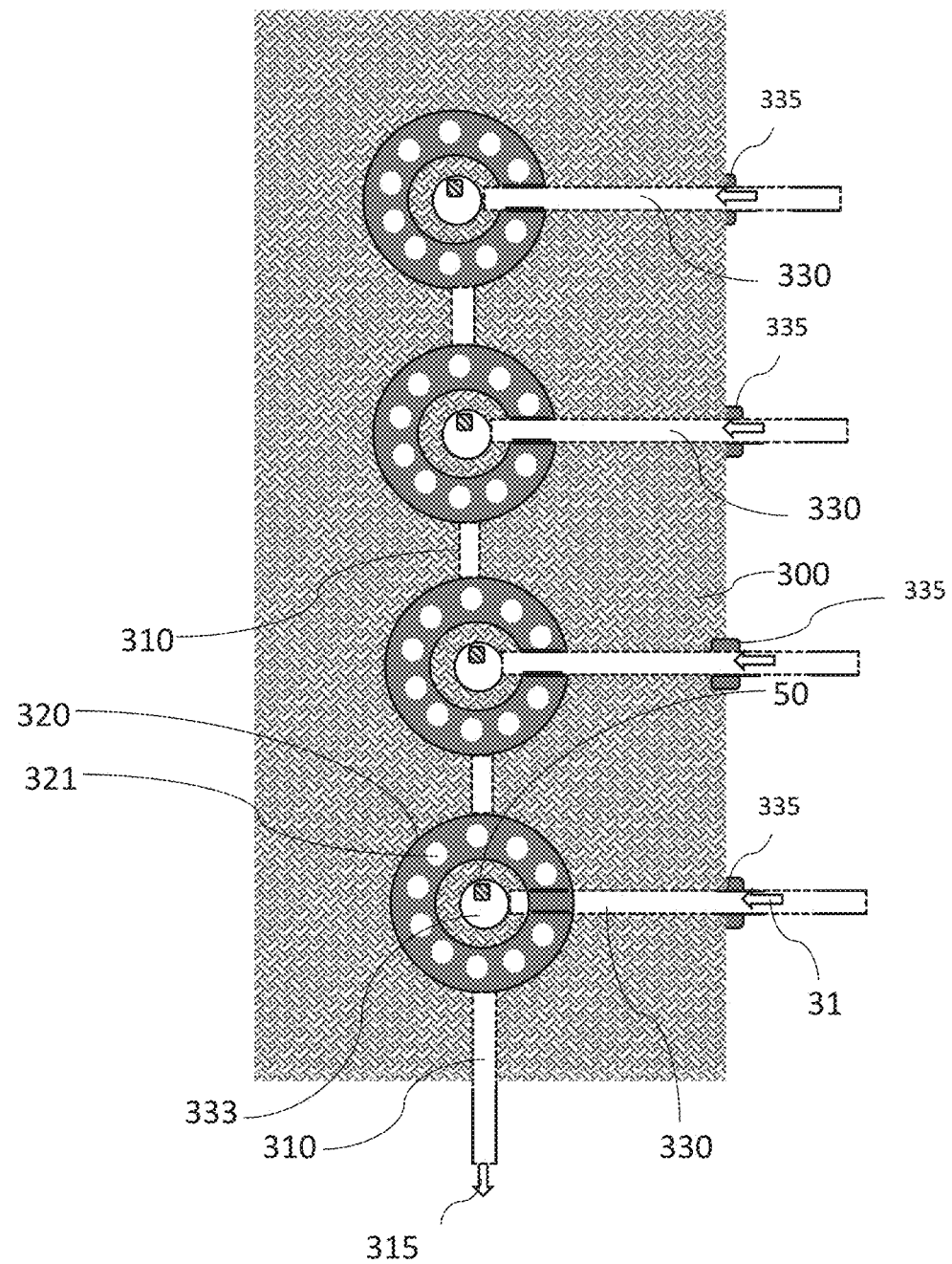
FIG. 10 shows a schematic top view of an embodiment of the present system.

Advantageously, a plurality of tests can be performed on the same organ 10, with the same or different $P_L$. In some embodiments, table 300 has a plurality of exit ports 333 which can be used for testing on a plurality of corresponding cored channels 20, as well as a plurality of vacuum ports 320 to immobilize organ 10. In some embodiments, there are 2,3,4,5,6, or more exit ports 333 and corresponding vacuum ports 320. Referring to FIG. 10, a schematic top view of an embodiment of the present system is presented, with table 300 having four vacuum ports 320 and four exit ports 333. These can be arranged in a linear fashion along table 300 as shown, or with slight curvature (not shown) to accommodate natural shape of organ 10. Each exit port 333 has a separate port 335 with optional valve (not shown) for supplying fluid supply channel 330 as needed during testing, including at different times, and at different pressures. Vacuum ports 320 can be all connected to the same vacuum channel 310 as shown, or to separate vacuum channels 310 each with optional valve (not shown). Each exit port 333 has its own pressure transducer, sensor, or detector 50. In most preferred embodiments, table 300 has 3, 4, or 5 vacuum ports 320 and exit ports 333, most preferably 5.

Referring to embodiments of FIGS. 7-10, in operation, application of vacuum to channel 310 results in vacuum assisted fixation of organ 10 on upper surface 312 of table 300 that then results in immobilizing of organ 10 for further testing. In some embodiments, a separate tubing (not shown) supplies blood directly into the artery and/or vein of organ 10, such as spleen, for organ 10 to be perfused prior to creating cored channel 20 so that the body of the organ 10 is not empty. This also acts as a secondary exit to allow lower pressure fluid to drain from the organ and which flow may be gated, to allow a natural state of inflation.

The vacuum fixation allows organ 10 to retain its natural (undistorted) shape, while holding cored channel 20 in alignment with fluid 30 infusion pathway i.e. with vertical portion 332 of channel 330 of table 300.

In operation, organ 10 is vacuum fixated on table 300, cored through to form cored channel 20 aligned and in registration with vertical portion 332, and the level of bleeding is set by supplying pressurized fluid 30 (such as blood) from perfusion system 200 via flow line 220 prior to application of the patch 100.

In operation, vacuum fixation of organ 10 on table 300 and circular knife alignment system (not shown) that is used to create cored channel 20, enables a tissue defect to be created consistently and ensures alignment of such defect (cored channel 20) with fluid 30 exit port 333 without distorting or crushing the tissue. Tissue fixation can be adjusted by increasing vacuum via vacuum port 320 applied to lower surface 12 of organ 10. The computer integrated data acquisition system enables measurement of the internal pressure of the ex-vivo model tissue in a consistent location within the vacuum fixation platform, directly below the hemostat pad.

In operation, patch 100 is then positioned on top surface 11 of organ 10 over cored channel 20 and a controlled tamponade force is applied on patch 100 either manually or preferably using a pressurized or spring-loaded ram fixture (not shown) to apply tamponade-like controlled and reproducible patch 100 application force. In addition to the function the tamponade fixture gives with respect to controllable, repeatable hemostatic pressure to the patch material, the tamponade fixture also serves a second function. After the test site has been taken to failure and the hemostatic material is dislodged, the plunger of the tamponade device is placed directly over the ruptured hemostat and once activated, provides direct mechanical compression of the defect, stopping the bleeding from that site, and allows for the next site to be tested without having to replace the solid organ.

Tamponade fixture can be automatically controlling application force, pressure, area, and contour (by using the piston), by using microprocessor, computer, feedback systems, or similar. For instance, pneumatic ram applies pressure to facilitate tamponade, with adjustable repeatable pressure by pneumatic control, switched on/off operation with dampers, tamponade after failure for next station, using interchangeable tamponade contours/materials.

In operation, pressure of the fluid 30 is fixed or is steadily increased (in a linear, stepped, pulsed, or prescribed manner) and local pressure $P_L$ is continuously monitored and or recorded, to detect failure or lack thereof of tested patch 100, such failure detected by a drop in $P_L$ when patch 100 detaches or delaminates from upper surface 11 of organ 10 and/or mechanically fails by e.g. forming a crack, a tear, a fissure in the patch itself. The maximum pressure to failure and or time to failure is then used to characterize the performance of the patch.

In operation, the present systems and methods enable evaluating hemostasis pad/patch/hydrogel type designs attributes such as application techniques, burst pressure, cohesive performance, adhesive performance, overlap region, and static and pulsed blood flow conditions.

A computer integrated data acquisition system is also provided (optional), enabling collection of local pressure ($P_L$) data as a function of time and detecting patch 100 failure as a function of pressure. Computer integrated data acquisition system can also, in some embodiments, control application of pressure and steady, stepped, pulsed or prescribed manner increase of pressure of pressurized fluid 30 from perfusion system 200 by controlling pumps, valves, elevation, and other fluid flow elements. The computer integrated data acquisition system enables measurement of the internal pressure of the ex-vivo model tissue in a consistent location within the vacuum fixation platform, directly below patch 100.

Alternatively, a wired transducer can be utilized, positioned on a rod having a sharp tip (not shown). For sealing purposes, the rod can have a coaxial porous tube surrounding such rod, configured for applying vacuum to said porous tube. The wired transducer is located close to the sharp tip. In operation, the rod is inserted into the organ until the wired transducer is positioned inside cored channel to measure local pressure. Detected failure of patch 100 or lack thereof is used to evaluate performance of patch 100 in vivo.

Wireless and RFID Pressure Measurement

Figure 11:
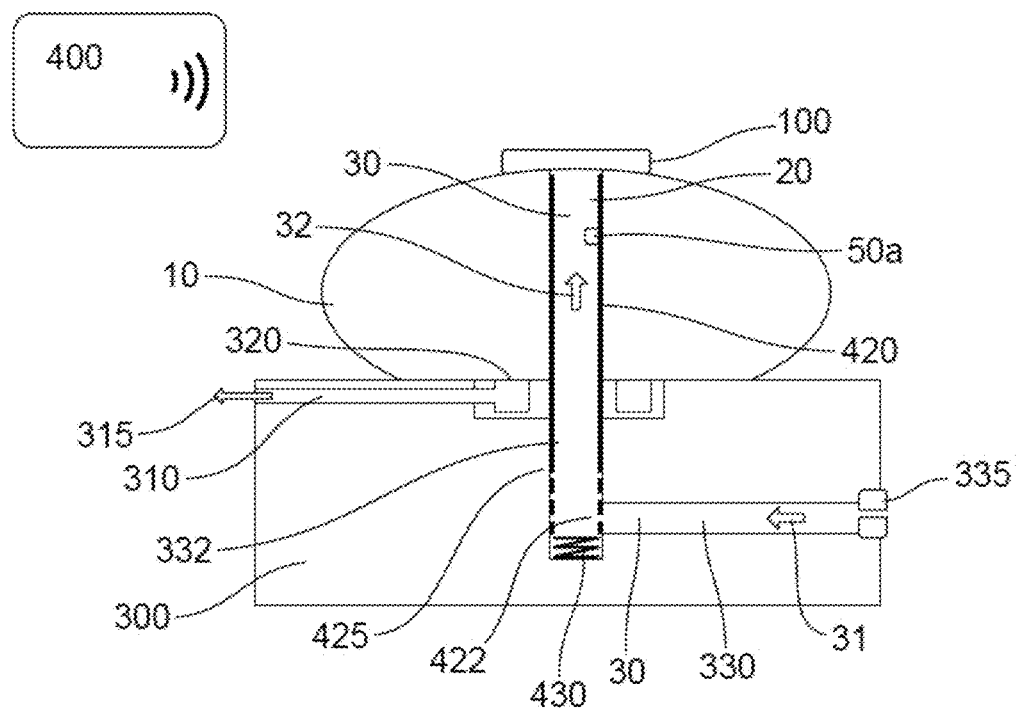
FIG. 11 shows a schematic side cross-sectional view of an embodiment of the present system.

Referring now to FIG. 11, an embodiment of the present invention is shown, with organ 10 fixated on table 300 using vacuum fixation as shown above. Pressure sensor 50a is positioned inside cored channel 20 in the immediate vicinity of patch 100. Pressure sensor 50a is a wireless pressure sensor/transmitter, configured to detect and measure local pressure and wirelessly report pressure in real time to wireless pressure reader or interrogator 400. Pressure sensor 50a and interrogator 400 can be, for example, RFID-based systems such as RFID pressure sensors/interrogators known to these skilled in the art.

According to the embodiment of FIG. 11, cored channel 20 is optionally lined with fluid-impermeable elongated hollow tubular liner 420, preferably made of water-insoluble polymer, such as polyethylene, polypropylene, PTFE, PVC, or similar, or made from metal, such as stainless steel. Tubular liner 420 outside diameter is sized to fit into cored channel 20 and into vertical portion 332 of channel 330. Lower end 425 of tubular liner 420 which is opposite to patch 100 has perforations or pores 422 that allow fluid 30 from channel 330 (arrow 31) to enter into tubular liner 420 and flow inside as shown by arrow 32 towards patch 100. Tubular liner 420 thus extends from inside table 300 and into most of organ 10 cored channel 20. Advantageously, tubular liner 420 prevents pressurized fluid 30 from escaping from cored channel 20 sideways, i.e. leaking through any blood vessels that cored channel 20 has intersected. Advantageously, tubular liner 420 helps to maintain the consistent pressure and avoid detrimental sideways leaks by keeping substantially all fluid 30 within cored channel 20.

An optional spring 430 is installed into vertical portion 332 of channel 330, contacting lower end 425 of tubular liner 420 to accommodate compression or expansion of organ 10 and application of controlled tamponade when applying patch 100 to organ 10.

Pressure sensor 50a can be attached to tubular liner 420 via any available means, such as adhesive, hook, fastener, bolt, pressure fit, magnetic attachment, or similar.

Operation of embodiments of FIG. 11 is similar to the previously described embodiments, with additional steps related to inserting tubular liner 420 into vertical portion 332 and into cored channel 20.

In Vivo Testing Systems and Methods

In Vivo Blind Cored Channel

Figure 12:
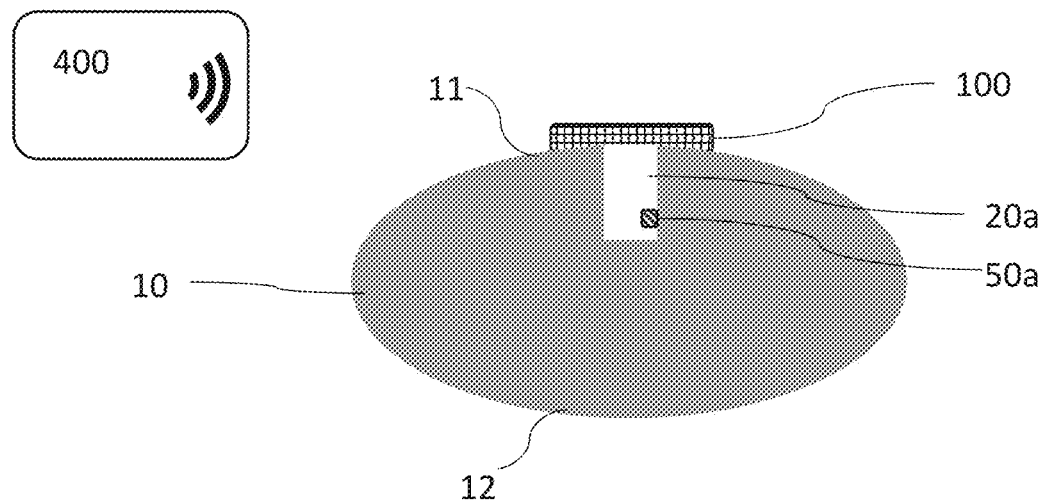
FIG. 12 shows a schematic side cross-sectional view of an embodiment of the present system.

Referring now to FIG. 12, an embodiment of the present invention is shown that enables one to perform testing in vivo using the animal natural blood flow (anticoagulated or not) and normal or pharmacologically augmented blood pressure. As shown, organ 10 in this embodiment is not fixated on table 300.

Blind cored channel 20a formed in organ 10 in vivo is formed so that it is not penetrating all of the organ 10 from lower surface 12 to top surface 11, but is formed as a blind channel penetrating from about 10% to about 90% of organ 10, such as 30%, 50%, 70% of organ 10, in some embodiments terminating from 10 mm to 50 mm from lower surface 12, such as 20 mm.

Pressure sensor 50a is positioned inside blind cored channel 20a by depositing pressure sensor 50a into blind cored channel 20a, sensor 50a is in the immediate vicinity of patch 100. Pressure sensor 50a is wireless pressure sensor/transmitter, configured to detect measure local pressure and wirelessly report pressure in real time to wireless pressure reader or interrogator 400.

In operation, organ 10 is in vivo cored to create blind cored channel 20a, pressure sensor 50a is deposited into blind cored channel 20a, patch 100 is applied, and pressure is wirelessly reported in real time to wireless pressure reader 400. Detected failure of patch 100 or lack thereof is used to evaluate performance of patch 100 in vivo.

In Vivo Blind Cored Channel and Pressurizing Cannula

Figure 13:
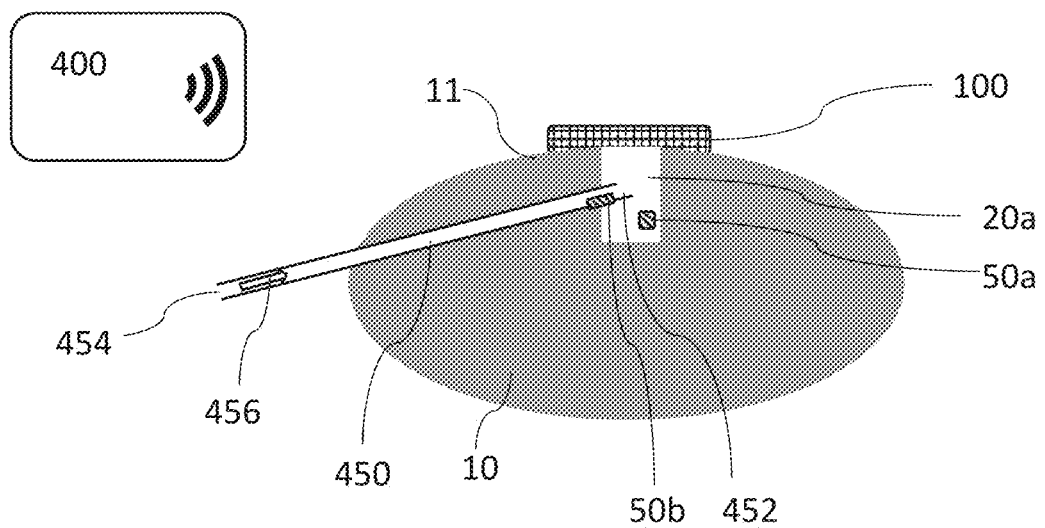
FIG. 13 shows a schematic side cross-sectional view of an embodiment of the present system.

Referring now to FIG. 13, an embodiment of the present invention is shown that enables one to perform testing in vivo similar to embodiment of FIG. 12, but with a capability of generating higher pressure for testing of patch 100 under higher stress conditions. Higher pressure than a natural pressure can be generated by pressurizing cannula or needle 450 that has a blood inlet 454 with blood flowing into cannula 450 as shown by arrow 456. Pressurizing cannula 450 can be supplied by pressurized blood by perfusion system, such as a peristaltic pump or gravity flow system (not shown).

Pressure sensor 50a is positioned inside blind cored channel 20a by depositing pressure sensor 50a into blind cored channel 20a so that it is in the immediate vicinity of patch 100. Alternatively, in some embodiments, pressure sensor 50b is attached to sharp tip 452 of pressurizing cannula 450 which is in operation inside blind cored channel 20a, whereby pressure sensor 50b is in the immediate vicinity of patch 100. Pressure sensors 50a, 50b are wired or wireless pressure sensors/transmitters, configured to detect measure local pressure and wirelessly report pressure in real time to wireless pressure reader or interrogator 400.

In operation, organ 10 is in vivo cored to create blind cored channel 20a, pressure sensor 50a is then optionally deposited into blind cored channel 20a, and patch 100 is applied. Further, prior or after patch 100 is applied, pressurizing cannula 450 is applied to organ 10 with sharp tip 452 penetrating organ 10 until sharp tip 452 enters into blind cored channel 20a.

Pressure in blind cored channel 20a is then maintained at higher than natural blood pressure levels using pressurized blood from perfusion system, to supply blood into pressurizing cannula 450 and thus into blind cored channel 20a, with either static (constant) pressure used, or steadily and/or step-wise increasing pressure used. Pressure is wirelessly reported in real time to wireless pressure reader 400 by sensor 50a or 50b. Detected failure of patch 100 or lack thereof is used to evaluate performance of patch 100 in vivo.

In Vivo Blind Cored Channel and Pressurizing Cannula with Vacuum Seal

Figure 14:
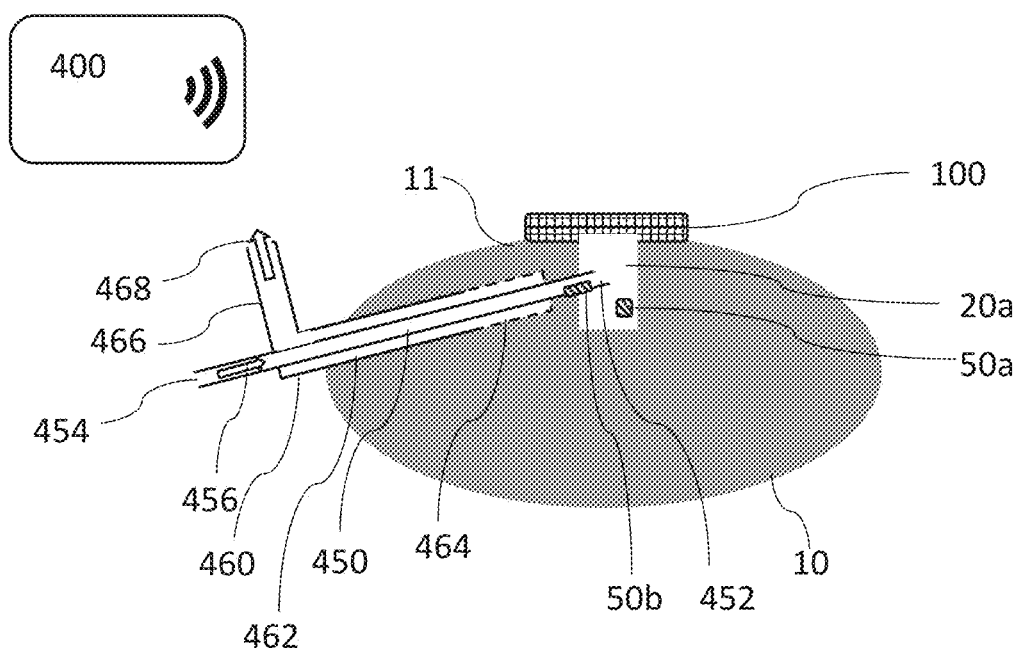
FIG. 14 shows a schematic side cross-sectional view of an embodiment of the present system.

Referring now to FIG. 14, an embodiment of the present invention similar to embodiments of FIG. 13 is shown, with pressurizing cannula 450 further having an external tube 460 maintained under vacuum for sealing organ 10 tissue around cannula 450. This arrangement enables a better sealing around cannula 450 to prevent leaks around cannula 450 under elevated pressures in blind cored channel 20a.

In this embodiment, external tube 460 is coaxial to cannula 450 and surrounds a portion of cannula 450 excluding sharp tip 452. Proximal end 466 of external tube 460 has a port 468 for connecting to vacuum source (not shown). A proximal portion 462 of external tube 460 that is outside of organ 10 and partially inside organ 10, but distal to sharp tip 452 is not perforated. A distal portion 464 of external tube 460 that is inside organ 10 and proximal to sharp tip 452 perforated having a plurality of small apertures, enabling application of vacuum to organ 10 where external tube 460 and pressurizing cannula 450 are inserted into organ 10. Advantageously, applying vacuum to external tube 460 enables better sealing around cannula 450 to prevent backflow leaks around cannula 450 under elevated pressures in blind cored channel 20a.

In operation, organ 10 is in vivo and is cored to create blind cored channel 20a, pressure sensor 50a is then optionally deposited into blind cored channel 20a, and patch 100 is applied. Further, prior or after patch 100 is applied, pressurizing cannula 450 is applied to organ 10 with sharp tip 452 penetrating organ 10 until sharp tip 452 enters into blind cored channel 20a. Alternatively to sensor 50a, pressure sensor 50b attached to sharp tip 452 of pressurizing cannula 450 can be used. Vacuum is applied to external tube 460 for sealing around cannula 450 to prevent backflow leaks around cannula 450 under elevated pressures in blind cored channel 20a.

Pressure in blind cored channel 20a is then maintained using pressurized blood from perfusion system, to supply blood into pressurizing cannula 450 and thus into blind cored channel 20a, with either static (constant) pressure used, or steadily/stepwise increasing pressure used. Pressure is wirelessly reported in real time to wireless pressure reader 400 by sensor 50a or 50b. Detected failure of patch 100 or lack thereof is used to evaluate performance of patch 100 in vivo.

In Vivo Blind Cored Channel and Pressurizing Cannula with Vacuum Seal and Liner

Figure 15:
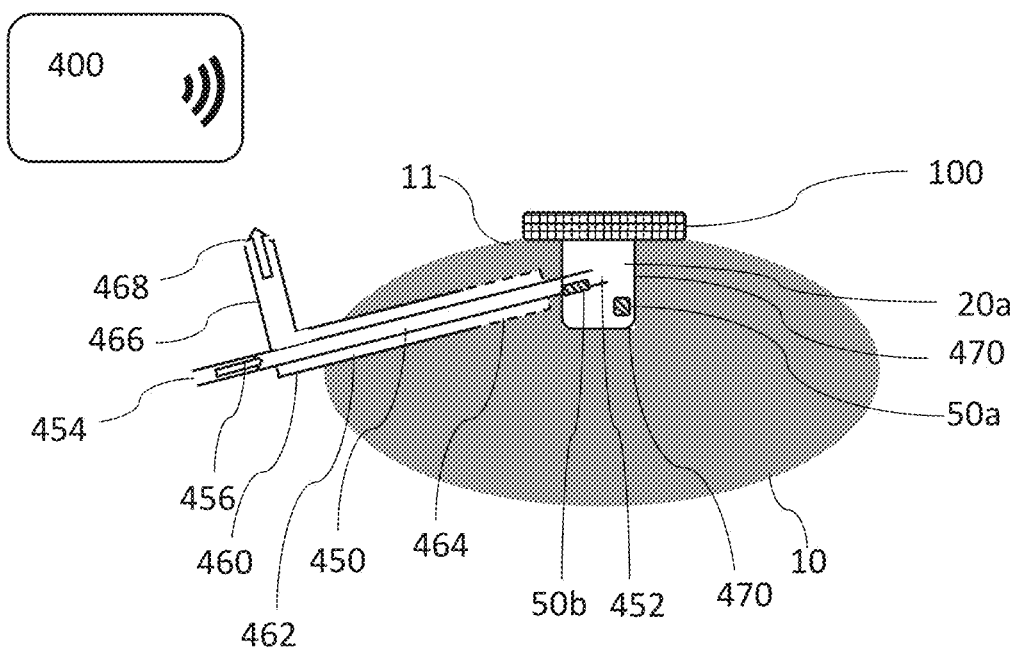
FIG. 15 shows a schematic side cross-sectional view of an embodiment of the present system.

Referring now to FIG. 15, an embodiment of the present invention similar to embodiments of FIG. 13, 14 is shown, further with a pierceable liner 470 inserted into blind cored channel 20a. Pierceable liner 470 is fluid-impermeable and is sized to fit into blind cored channel 20a and is made of thin polymeric material, such as polyethylene, polypropylene, PTFE, PVC, or similar.

Advantageously, pierceable liner 470 prevents pressurized fluid 30 from escaping from blind cored channel 20a sideways, i.e. leaking through any blood vessels that blind cored channel 20a has intersected. Advantageously, pierceable liner 470 helps to maintain the consistent pressure and avoid detrimental sideways leaks by keeping substantially all fluid 30 within blind cored channel 20a.

While embodiment having pressurizing cannula 450 with external tube 460 is shown in FIG. 15, pressurizing cannula 450 without external tube 460 similar to FIG. 13 an also be utilized (not shown) with pierceable liner 470.

In operation, organ 10 is in vivo cored to create blind cored channel 20a, and pierceable liner 470 inserted into blind cored channel 20a. Pressure sensor 50a is optionally deposited into blind cored channel 20a, and patch 100 is applied. Alternatively to sensor 50a, pressure sensor 50b attached to sharp tip 452 of pressurizing cannula 450 can be used. Further, prior or after patch 100 is applied, pressurizing cannula 450 is applied to organ 10 with sharp tip 452 penetrating organ 10 until sharp tip 452 piercing pierceable liner 470 and enters into blind cored channel 20a. Vacuum is then applied to external tube 460 for sealing around cannula 450 to prevent backflow leaks around cannula 450 under elevated pressures in blind cored channel 20a.

Pressure in blind cored channel 20a is then maintained using pressurized blood from perfusion system, to supply blood into pressurizing cannula 450 and thus into blind cored channel 20a, with either static (constant) pressure used, or steadily/stepwise increasing pressure used. Pressure is wirelessly reported in real time to wireless pressure reader 400 by sensor 50a or 50b.

Alternatively, a wired transducer can be utilized, positioned on a rod having a sharp tip (not shown). For sealing purposes, the rod can have a coaxial porous tube surrounding such rod, configured for applying vacuum to said porous tube. The wired transducer is located close to the sharp tip. In operation, the rod is inserted into the organ until the wired transducer is positioned inside blind cored channel to measure local pressure. Detected failure of patch 100 or lack thereof is used to evaluate performance of patch 100 in vivo.

Figure 16:
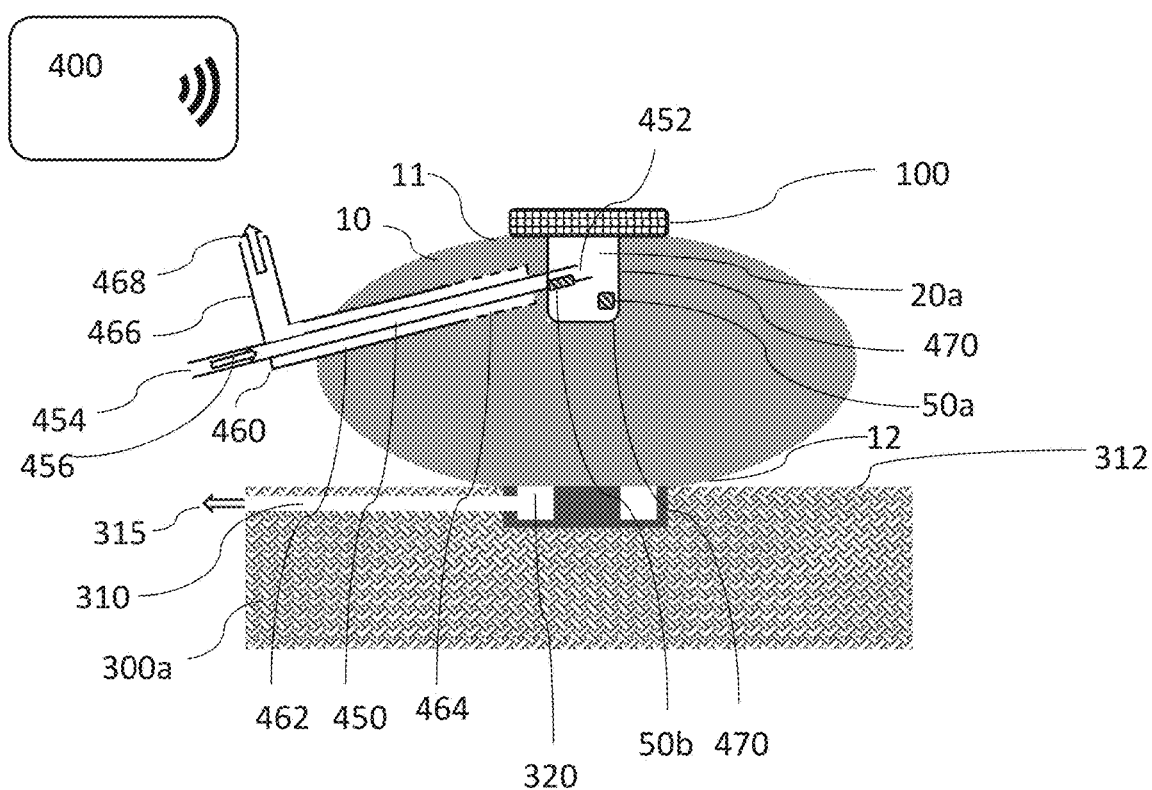
FIG. 16 shows a schematic side cross-sectional view of an embodiment of the present system.

Ex Vivo Blind Cored Channel with Pressurizing Cannula, Optionally with Vacuum Seal and Liner Referring now to FIG. 16, an embodiment of the present invention similar to in vivo embodiments with a blind cored channel 20a of FIGS. 12, 13, 14, 15 is shown, applying similar structures and methods to ex vivo testing, with fixation of organ 10 similar to embodiments of FIGS. 7-11 with vacuum fixation table 300.

As shown in FIG. 16, organ 10 is fixated on vacuum fixation table 300a with vacuum applied to vacuum channel 310 as shown by evacuation arrow 315, with vacuum port 320 in contact with lower surface 12 of organ 10. Table 300a has no fluid supply channel connected to perfusion system, no fluid 30 exit port 333. Instead fluid is supplied into blind cored channel 20a by pressurizing cannula 450. Similar to embodiments of FIGS. 12-15, blind cored channel 20a is not penetrating all of the organ 10 from lower surface 12 to top surface 11, but is formed as a blind channel penetrating from about 10% to about 90% of organ 10, such as 30%, 50%, 70% of organ 10.

Similar to embodiments of FIGS. 13-15, higher pressure than a natural pressure can be generated by pressurizing cannula or needle 450 that has a blood inlet 454 with blood flowing into cannula 450 as shown by arrow 456. Pressurizing cannula 450 can be supplied by pressurized blood by perfusion system, such as a peristaltic pump or gravity flow system (not shown).

Similar to embodiments of FIGS. 14-15, pressurizing cannula 450 can optionally be supplied with an external tube 460 maintained under vacuum for sealing around cannula 450. This arrangement enables a better sealing around cannula 450 to prevent leaks around cannula 450 under elevated pressures in blind cored channel 20a. Advantageously, applying vacuum to external tube 460 enables better sealing around cannula 450 to prevent backflow leaks around cannula 450 under elevated pressures in blind cored channel 20a.

Similar to embodiments of FIG. 15, a pierceable liner 470 can be optionally inserted into blind cored channel 20a. Pierceable liner 470 is fluid-impermeable and is sized to fit into blind cored channel 20a and is made of thin polymeric material, such as polyethylene, polypropylene, PTFE, PVC, or similar. Advantageously, pierceable liner 470 prevents pressurized fluid 30 from escaping from blind cored channel 20a sideways, i.e. leaking through any blood vessels that blind cored channel 20*a* has intersected. Advantageously, pierceable liner 470 helps to maintain the consistent pressure and avoid detrimental sideways leaks by keeping substantially all fluid 30 within blind cored channel 20*a*.

Pressure sensor 50*a* is positioned inside blind cored channel 20*a* by depositing pressure sensor 50*a* into blind cored channel 20*a* and is in the immediate vicinity of patch 100.

In some embodiments, pressure sensor 50*b* is attached to sharp tip 452 of pressurizing cannula 450 which is inside blind cored channel 20*a*, whereby pressure sensor 50*b* is in the immediate vicinity of patch 100. Pressure sensors 50*a*, 50*b* are wireless pressure sensors/transmitters, configured to detect measure local pressure and wirelessly report pressure in real time to wireless pressure reader or interrogator 400. Alternatively, 50*b* can be a wired pressure transducer. Alternatively, a wired transducer can be utilized, positioned on a rod having a sharp tip (not shown). For sealing purposes, the rod can have a coaxial porous tube surrounding such rod, configured for applying vacuum to said porous tube. The wired transducer is located close to the sharp tip. In operation, the rod is inserted into the organ until the wired transducer is positioned inside blind cored channel to measure local pressure. Detected failure of patch 100 or lack thereof is used to evaluate performance of patch 100 in vivo.

In some embodiments, pressure sensor can be attached to a special dedicated sensor cannula with piercing tip (not shown) and introduced independently into the cored channel or blind cored channel.

In some embodiments, wired or wireless pressure sensor can be utilized not only to read and report pressure, but also to control applied fluid pressure wherein pressure source can supply variable pressure based on pressure at $P_L$), utilizing computer-controlled feedback, microprocessor control, software, or similar, or combinations thereof.

In operation, organ 10 is ex vivo is cored to create blind cored channel 20*a*. An optional pierceable liner 470 is inserted into blind cored channel 20*a*. Pressurizing cannula 450 with or without external tube 460 is applied to organ 10 with sharp tip 452 penetrating organ 10 until sharp tip 452 enters into blind cored channel 20*a*. Optional vacuum is then applied to optional external tube 460 for sealing around cannula 450 to prevent backflow leaks around cannula 450 under elevated pressures in blind cored channel 20*a*. Pressure sensor 50*a* is optionally deposited into blind cored channel 20*a*. Pressure sensor 50*b* is optionally attached to sharp tip 452 of pressurizing cannula 450. Patch 100 is applied over blind cored channel 20*a*. Pressure in blind cored channel 20*a* is then maintained using pressurized blood from perfusion system, to supply blood into pressurizing cannula 450 and thus into blind cored channel 20*a*, with either static (constant) pressure used, or steadily/stepwise increasing pressure used. Pressure is wirelessly reported in real time to wireless pressure reader 400 by sensor 50*a* or 50*b*. Detected failure of patch 100 or lack thereof is used to evaluate performance of patch 100 ex vivo.

It should be understood that the foregoing disclosure and description of the embodiments of the present invention are illustrative and explanatory thereof and various changes in the size, shape and materials as well as in the description of the preferred embodiment may be made without departing from the spirit of the invention.

We claim:

1. A system for ex vivo testing performance of a hemostatic or sealing product attached to an animal organ and fully covering a cored channel in said organ, comprising:

a) a pressure sensor positioned proximate to said hemostatic or sealing product in said cored channel;
   b) a monitoring or recording device configured to receive pressure readings from said pressure sensor; and
   c) a pressurized fluid source connected to said cored channel and configured to supply said pressurized fluid into said cored channel under constant or variable pressure.

2. The system of claim 1, wherein said pressure sensor and said monitoring or recording device are wireless.

3. The system of claim 1, wherein said pressure sensor and said monitoring or recording device are connected by an electric cable.

4. The system of claim 1, wherein said pressure sensor is positioned within 30 mm of said hemostatic or sealing product.

5. The system of claim 1, wherein said pressurized fluid source comprises a perfusion system that is a peristaltic pump or gravity fed system.

6. The system of claim 1, wherein said pressurized fluid is blood and wherein said organ comprises liver, spleen, or kidney.

7. The system of claim 1, further comprising a vacuum fixation table comprising:

a) a body having a flat, contoured, or conformable upper surface and
   b) a vacuum channel within said body, said vacuum channel connected to a source of vacuum and terminating in a vacuum port on said upper surface, said vacuum port comprising one or more orifices or apertures on said upper surface;
   said body further comprising a fluid supply channel within said body that is connected to said pressurized fluid source and wherein said fluid supply channel terminates on said upper surface with a fluid exit port that is surrounded by said vacuum port.

8. The system of claim 7, wherein said vacuum fixation table comprises a plurality of said vacuum ports and plurality of said fluid exit ports.

9. The system of claim 7, wherein said cored channel is lined with a fluid-impermeable elongated hollow tubular liner sized to fit into said cored channel and into a portion of said fluid supply channel, with an optional spring installed into said fluid supply channel contacting said tubular liner.

10. The system of claim 1, further comprising a vacuum fixation table comprising:

a) a body having a flat, contoured, or conformable upper surface and
    b) a vacuum channel within said body,
    said vacuum channel connected to a source of vacuum and terminating in a vacuum port on said upper surface,
    said vacuum port comprising one or more orifices or apertures on said upper surface;
    wherein said system further comprises a pressurizing cannula connected to said pressurized fluid source and terminating with a sharp tip, and
    wherein said cored channel is a blind cored channel and said sensor is wireless.

11. The system of claim 10,
    wherein said pressure sensor is positioned inside blind cored channel as a stand-alone unit or is attached to said pressurizing cannula proximate to said sharp tip.

12. The system of claim 10, wherein said pressurizing cannula further comprises:

a) an external tube that is coaxial and surrounds a portion of said pressurizing cannula;

said external tube is connected to a source of vacuum, wherein a distal portion of said external tube proximal to said sharp tip is perforated.

13. The system of claim 10, wherein said blind cored channel is lined with a pierceable liner.

14. A system for in vivo testing performance of a hemostatic or sealing product attached to an animal organ and fully covering a blind cored channel in said organ, comprising:
   a) a pressurizing cannula connected to a pressurized fluid source and terminating with a sharp tip,
   b) a wireless or wired pressure sensor positioned proximate to said hemostatic or sealing product inside said blind cored channel as a stand-alone unit or attached to said pressurizing cannula proximate to said sharp tip,
   c) a monitoring or recording device configured to receive pressure readings from said pressure sensor.

15. The system of claim 14, wherein said pressurizing cannula further comprises:
   a) an external tube that is coaxial and surrounds a portion of said pressurizing cannula;

said external tube is connected to a source of vacuum, wherein a distal portion of said external tube proximal to said sharp tip is perforated.

16. The system of claim 14, wherein said blind cored channel is lined with a pierceable liner.

\* \* \* \* \*